United States Patent [19]

Prosser

[11] Patent Number: 5,246,002
[45] Date of Patent: Sep. 21, 1993

[54] NOISE INSENSITIVE PULSE TRANSMITTANCE OXIMETER

[75] Inventor: Stephen J. Prosser, Bothell, Wash.

[73] Assignee: Physio-Control Corporation, Redmond, Wash.

[21] Appl. No.: 833,930

[22] Filed: Feb. 11, 1992

[51] Int. Cl.$^5$ .............................................. A61B 5/00
[52] U.S. Cl. ...................................... 128/633; 356/41
[58] Field of Search ............... 128/633, 634, 664, 665; 356/41

[56] References Cited

U.S. PATENT DOCUMENTS

| | | | |
|---|---|---|---|
| 4,407,290 | 10/1983 | Wilber | 128/633 |
| 4,569,589 | 2/1986 | Neufeld | 356/39 |
| 4,846,183 | 7/1989 | Martin | 128/633 |
| 4,859,057 | 8/1989 | Taylor et al. | 356/41 |
| 4,863,265 | 9/1989 | Flower et al. | 128/633 |
| 4,869,254 | 9/1989 | Stone et al. | 128/633 |
| 4,934,372 | 6/1990 | Corenman et al. | 128/633 |
| 4,942,877 | 7/1990 | Sakai et al. | 128/633 |
| 5,058,588 | 10/1991 | Kaestle | 128/633 |
| 5,099,123 | 3/1992 | Harjunmaa | 250/345 |
| 5,137,023 | 8/1992 | Mendelson et al. | 128/633 |

Primary Examiner—Lee S. Cohen
Assistant Examiner—Kevin Pontius
Attorney, Agent, or Firm—Christensen, O'Connor, Johnson & Kindness

[57] ABSTRACT

A noise insensitive pulse transmittance oximeter (11) is disclosed. Two LEDs (21 and 23) are included in the pulse transmittance oximeter. The LEDs alternately emit a red light pulse and an infrared light pulse. A detector (13) detects corresponding red transmittance pulses and infrared transmittance pulses that are indicative of the amount of light transmitted through tissue having blood flowing therein. A microprocesser (29) determines the peak and valley values of the red transmittance pulses and infrared transmittance pulses over a cycle. The difference between the peak and valley values for the red transmittance pulses and infrared transmittance pulses are calculated by the microprocessor. The microprocessor generates control signals that vary the intensity of the LEDs until the differences between the peak and valley values of the red transmittance pulses and infrared transmittance pulses are substantially equal.

18 Claims, 6 Drawing Sheets

NOISE INSENSITIVE PULSE TRANSMITTANCE OXIMETER

FIELD OF THE INVENTION

The invention relates to the field of oximetry and, more particularly, to a noise insensitive pulse transmittance oximeter.

BACKGROUND OF THE INVENTION

It is known that various blood parameters may be calculated by measuring the transmittance of light at different wavelengths through tissue having blood flowing therein. Examples of such blood parameters include carbon monoxide, carbon dioxide, glucose, and oxygen concentrations. Accurate information on these blood parameters may be important for a variety of reasons. For example, in the operating room, up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

The non-invasive technique of measuring light transmittance in order to formulate blood parameter information is desirable in many applications for reasons of operator convenience and patient comfort. One well known technique that determines oxygen saturation in blood is pulse transmittance oximetry. The technique generally involves measuring the transmittance of light through body tissue at two different wavelengths. Typically, the two wavelengths are in the red and infrared regions. The measurements are made at both systolic pressure and diastolic pressure. In one known formulation, an oxygen saturation ratio is given by:

$$R_{OS} = \frac{\ln\left(\frac{R_H}{R_L}\right)}{\ln\left(\frac{IR_H}{IR_L}\right)} \tag{1}$$

where $R_{OS}$ is the oxygen saturation ratio, $R_L$ is the transmittance of light at the red wavelength at systolic pressure, $R_H$ is the transmittance of light at the red wavelength at diastolic pressure, $IR_L$ is the transmittance of light at the infrared wavelength at systolic pressure, and $IR_H$ is the transmittance of light at the infrared wavelength at diastolic pressure. Oxygen saturation may then be ascertained from the $R_{OS}$ value using empirically derived calibration curves. The precise description of the method and apparatus for measuring the transmittance of light is not part of the present invention and so is described here only generally. Reference to U.S. Pat. No. 4,819,646 to Cheung et al. is recommended for a detailed description of pulse transmittance oximetry.

The accuracy of $R_{OS}$ is dependent therefore on the accuracy of the measurements of the transmittance of light at both wavelengths and at both systolic and diastolic pressure. The transmittance of light measurements are detected typically by a photodiode. One significant difficulty with transmittance of light measurements is the introduction of noise. Noise may originate from several sources including, but not limited to: preamplifier noise, induced noise from inside the oximeter, induced noise from outside the oximeter, and ambient light noise.

The present invention provides a pulse transmittance oximeter that is insensitive to noise.

SUMMARY OF THE INVENTION

A noise insensitive pulse transmittance oximeter is disclosed. The pulse transmittance oximeter includes a red LED and infrared LED. The red LED and infrared LED emit a plurality of red light pulses and an infrared light pulses in alternating sequence. The red light pulses and infrared light pulses are transmitted through tissue having blood flowing therein. A detector provides corresponding red transmittance pulses and infrared transmittance pulses, the red and infrared transmittance pulses indicative of the amount of red light and infrared light transmitted through the tissue, respectively. A microprocessor determines the peak and valley values of the red transmittance pulses and infrared transmittance pulses over one cyclic period. The difference between the peak and valley values for the red transmittance pulses and infrared transmittance pulses are calculated by the microprocessor.

In the preferred embodiment, the microprocessor generates control signals that vary the intensity of the LEDs until the difference between the peak and valley values of the red transmittance pulses and infrared transmittance pulses are equal.

In an alternative embodiment, the microprocessor generates control signals that vary the intensity of the LEDs until the ratio of the difference between the peak and valley values of the red transmittance pulses and the difference between the peak and valley values of the infrared transmittance pulses is equal to a noise ratio. The noise ratio is the ratio of the noise in the red transmittance pulses and the infrared transmittance pulses.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
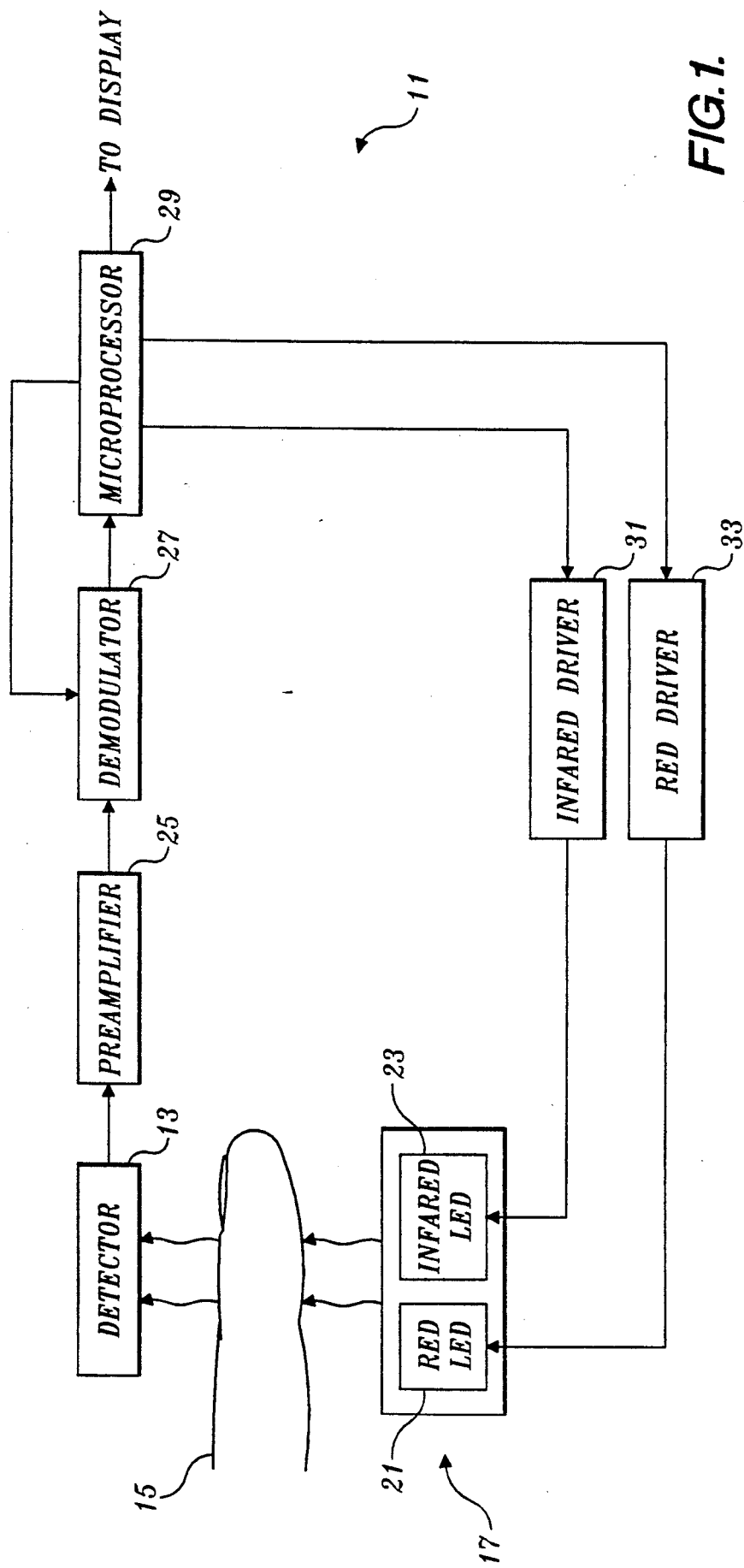
FIG. 1 is a block diagram of a pulse transmittance oximeter.

Referring to FIG. 1, a pulse transmittance oximeter 11 formed in accordance with the present invention is seen. Pulse transmittance oximeter 11 comprises a light source 17, a detector 13, a preamplifier 25, a demodulator 27, a microprocessor 29, a red driver 33, and an infrared driver 31. The light source 17 includes a red LED 21 and an infrared LED 23. Red LED 21 produces red light in the red region of the electromagnetic spectrum. Infrared LED 23 produces infrared light in the infrared region of the electromagnetic spectrum.

In operation, microprocessor 29 supplies red control signals to red driver 33 and infrared control signals to infrared driver 31. The red control signals and the infrared control signals are transmitted in alternating sequence such that when a red control signal is being transmitted by microprocessor 29, an infrared control signal is not being transmitted. Similarly, when an infrared control signal is being transmitted by microprocessor 29, a red control signal is not being transmitted. In the preferred embodiment, microprocessor 29 transmits 960 red control signals and 960 infrared control signals in alternating sequence every second. Thus, the pulse transmittance oximeter 11 is said to operate at 960 Hz. Each time a red control signal is received by red driver 33, red driver 33 produces a red driving current $D_R$ that is transmitted to red LED 21. The red driving current $D_R$ causes red LED 21 to emit a pulse of red light. Similarly, each time an infrared control signal is received by infrared driver 31, infrared driver 31 produces an infrared driving current $D_{IR}$ that is transmitted to infrared LED 23. The infrared driving current $D_{IR}$ causes infrared LED 23 to emit a pulse of infrared light. Thus, the control signals cause the drivers 31 and 33 to produce driving currents that cause LEDs 21 and 23 to emit a pulse of light.

Moreover, both the red and infrared control signals has integrated therein a magnitude signal that determines the magnitude of the driving currents $D_R$ and $D_{IR}$ produced by the drivers 31 and 33. The magnitude signal is integrated into each control signals by microprocessor 29. The magnitude of the driving currents $D_R$ and $D_{IR}$ supplied by drivers 31 and 33 to the LEDs determines the intensity of the pulses of light that are output. The larger the driving current supplied to the LEDs, the greater the intensity of the pulses of light produced. In the preferred embodiment, the LEDs utilized respond linearly to the driving current. For example, if the driving current is doubled, the intensity of the light produced by the LED is doubled. Thus, the microprocessor 29 can directly and accurately control the intensity of the pulses of light output by the LEDs by controlling the formulation of the magnitude signal that is integrated to each control signal. Conversely, the intensity of the pulses of light output by the LEDs can be determined at microprocessor 29 by examining the magnitude signal of the control signal that triggered the pulses of light.

The pulses of red light and the pulses of infrared light are directed towards and transmitted through tissue having blood flowing therein, such as a finger 15. The pulses of red light and the pulses of infrared light that are transmitted through finger 15 are received by detector 13 as red transmittance pulses and infrared transmittance pulses, respectively. In turn, detector 13 provides an output signal that is indicative of the intensity of the red transmittance pulses and infrared transmittance pulses incident thereon. Because of the alternating sequence of the pulses of red light and pulses of infrared light, the output signal provided by detector 13 is an alternating sequence of red transmittance pulses and infrared transmittance pulses.

Figure 2:
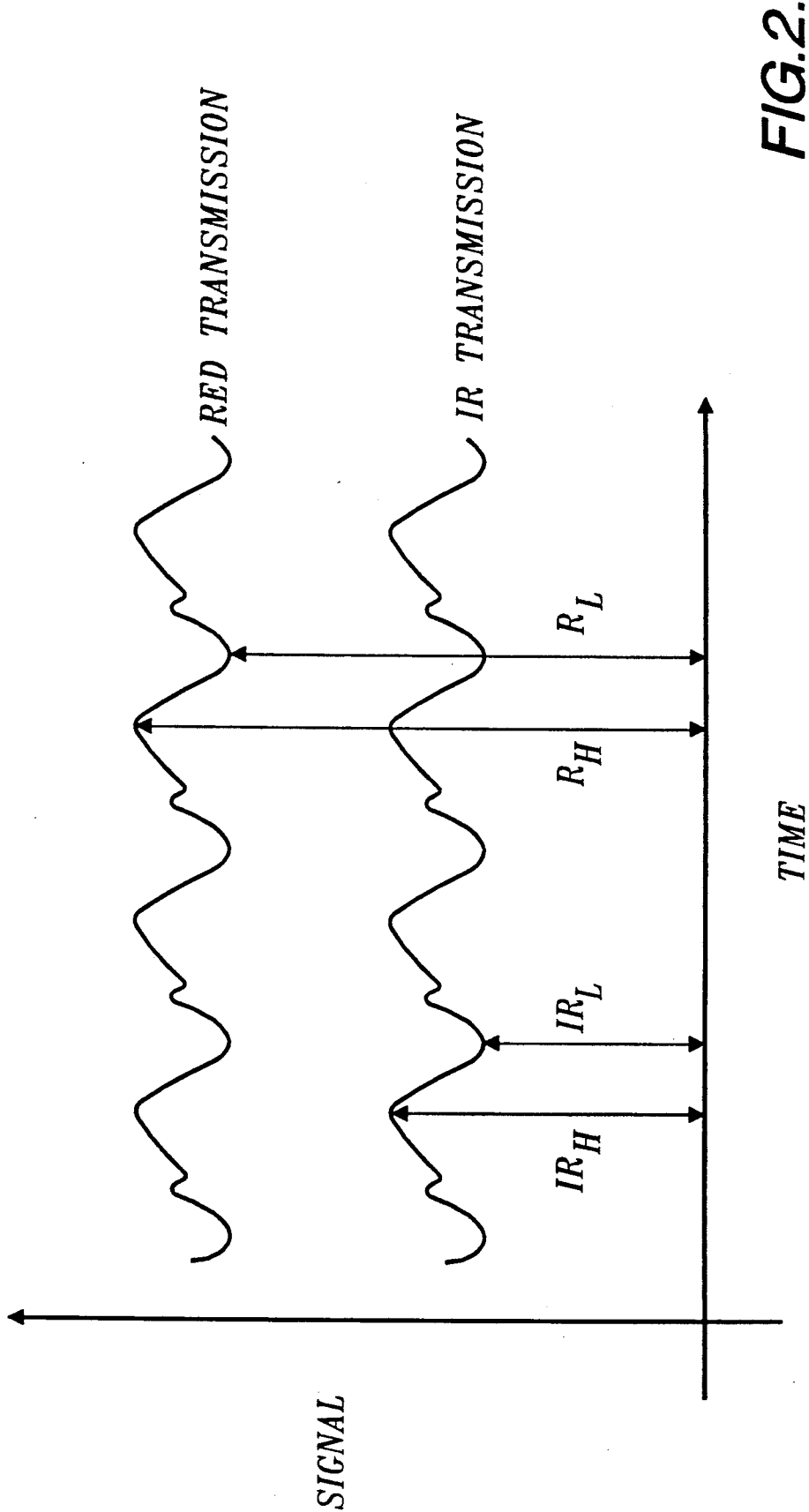
FIG. 2 is a graphical plot as a function of time of the transmittance of light at the red and infrared wavelengths through the finger.

The output signal produced by detector 13 is provided to preamplifier 25 which serves to amplify the output signal. The output of preamplifier 25 is supplied to demodulator 27 as a demodulator input signal. Demodulator 27 operates to produce the red and infrared transmission waveforms shown in FIG. 2 from the alternating sequence of red transmittance pulses and infrared transmittance pulses provided by detector 13 via preamplifier 25. Although the red and infrared waveforms of FIG. 2 are shown as continuous, the waveforms are comprised of a series of discrete values. Each discrete value corresponds to a single red or infrared transmittance pulse. For clarity however, the discrete values have been connected so as to form the continuous red and infrared waveforms of FIG. 2.

In the preferred embodiment, demodulator 27 includes a red sample and hold circuit that responds to the red transmittance pulses produced by detector 13. Further, demodulator 27 also includes an infrared sample and hold circuit that responds to the infrared transmittance pulses produced by detector 13. The timing of the red and infrared sample and hold circuits is controlled by demodulator control signals transmitted by microprocessor 29. The demodulator control signals are generally operative to activate the red sample and hold during the portion of the demodulator input signal that corresponds to the red transmittance pulse. The demodulator control signals are also generally operative to activate the infrared sample and hold during the portion of the demodulator input signal that corresponds to the infrared transmittance pulse. In this manner, the red transmittance pulses and the infrared transmittance pulses are "separated" from one another to provide the red and infrared transmission waveforms of FIG. 2.

The red and infrared transmission waveforms, plotted as a function of time, are cyclical. The cyclic nature of the red and infrared transmission waveforms is indicative of the periodic change of blood volume in the tissue of finger 15. The changing blood volume is caused by the beating of the heart of the human being. Specifically, during systolic pressure, the blood volume in the finger 15 is at its highest. Therefore, the transmittance of light is at a low point, corresponding to a low output signal from detector 13. Conversely, during diastolic pressure, the blood volume in the finger is at its lowest. Therefore, the transmittance of light is at a high point, corresponding to a high output signal from detector 13. It can be appreciated that systolic pressure and diastolic pressure occurs once every heartbeat. Thus, the cyclic nature of the red and infrared transmission waveforms is due generally to the cyclic heartbeat of the human being. Moreover, each cycle of the transmission waveforms correspond to one heartbeat.

As seen in FIG. 2, the light transmittance at systolic pressure for the red light is denoted $R_L$, while the light transmittance at diastolic pressure for the red light is denoted $R_H$. Analogously, the light transmittance at systolic pressure for the infrared light is denoted $IR_L$, while the light transmittance at diastolic pressure for the infrared light is denoted $IR_H$. Note that in FIG. 2, for clarity, $IR_L$ and $IR_H$ are shown on a different cyclic period of the waveforms that $R_L$ and $R_H$. However, if the red transmission waveforms and infrared transmission waveforms are superimposed upon one another, for the same cyclic period, it would be apparent that $R_H$ and $IR_H$ occur at substantially the same instant of time, since both $R_H$ and $IR_H$ are defined to occur during systolic pressure. Similarly, $R_L$ and $IR_L$ also occur at substantially the same instant of time, since both $R_L$ and $IR_L$ are defined to occur during diastolic pressure.

The red and infrared transmission waveforms of FIG. 2 are provided to microprocessor 29. Microprocessor 29 formulates the red and infrared control signals that are sent to the drivers 31 and 33. The magnitude signal component of the control signals are based upon the values of $R_H$, $R_L$, $IR_H$, and $IR_L$ in the transmission waveforms. Specifically, microprocessor 29: (1) normalizes the red and/or infrared transmission waveforms to remove any discontinuities caused by adjusting the intensity of the pulses of light output from red LED 21 or infrared LED 23, (2) filters the red and infrared transmission waveforms, (3) uses peak detection software to determine the values of $R_H$, $R_L$, $IR_H$, and $IR_L$, (4) denormalizes the values of $R_H$, $R_L$, $IR_H$, and $IR_L$, and (5) formulates the magnitude signals in accordance with the method of the present invention, and thus, adjusts the intensity of light output from red LED 21 and infrared LED 23.

Figure 3:
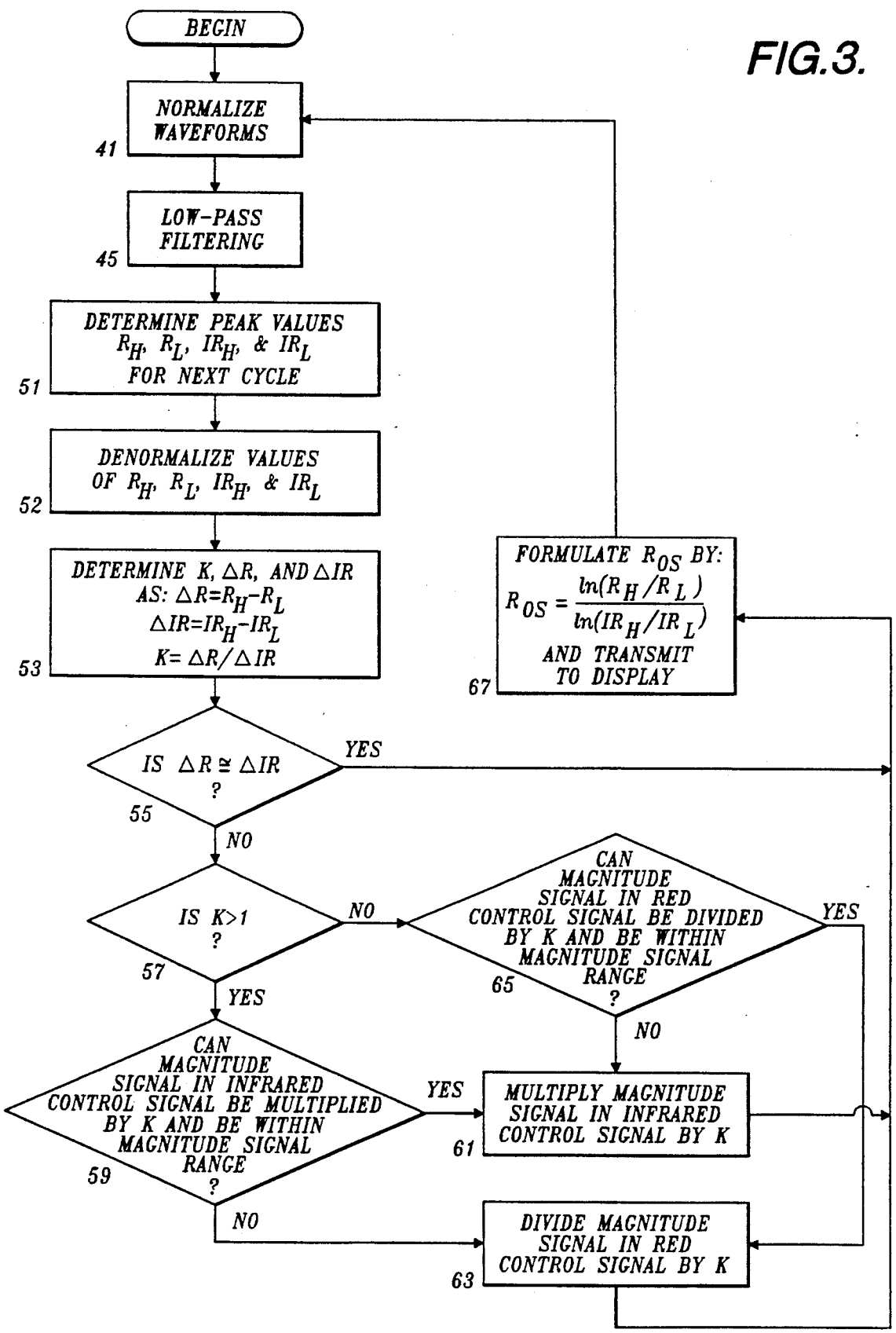
FIG. 3 is a flow chart illustrating the preferred method of the present invention.

FIG. 3 illustrates the operation of microprocessor 29. In particular, following receipt of the red and infrared transmission waveforms of FIG. 2, at a box 41, the received red and/or infrared transmission waveforms are normalized to remove any discontinuities in the signal. As will be seen in greater detail below, the intensity of the pulses of light output from red LED 21 or infrared LED 23 may be varied. As noted above, the intensity of the pulses of light output from the LEDs is dependant upon the magnitude signal component of the red and infrared control signals produced by microprocessor 29. The variation of the intensity of the pulses of light output by the red or infrared LEDs tend to produce discontinuities in the corresponding red or infrared transmission waveforms. In turn, the discontinuities caused by the adjustments to the LEDs tend to disrupt the operation of the low-pass filtering, at box 45, of the red and infrared transmission waveforms.

Figure 4:
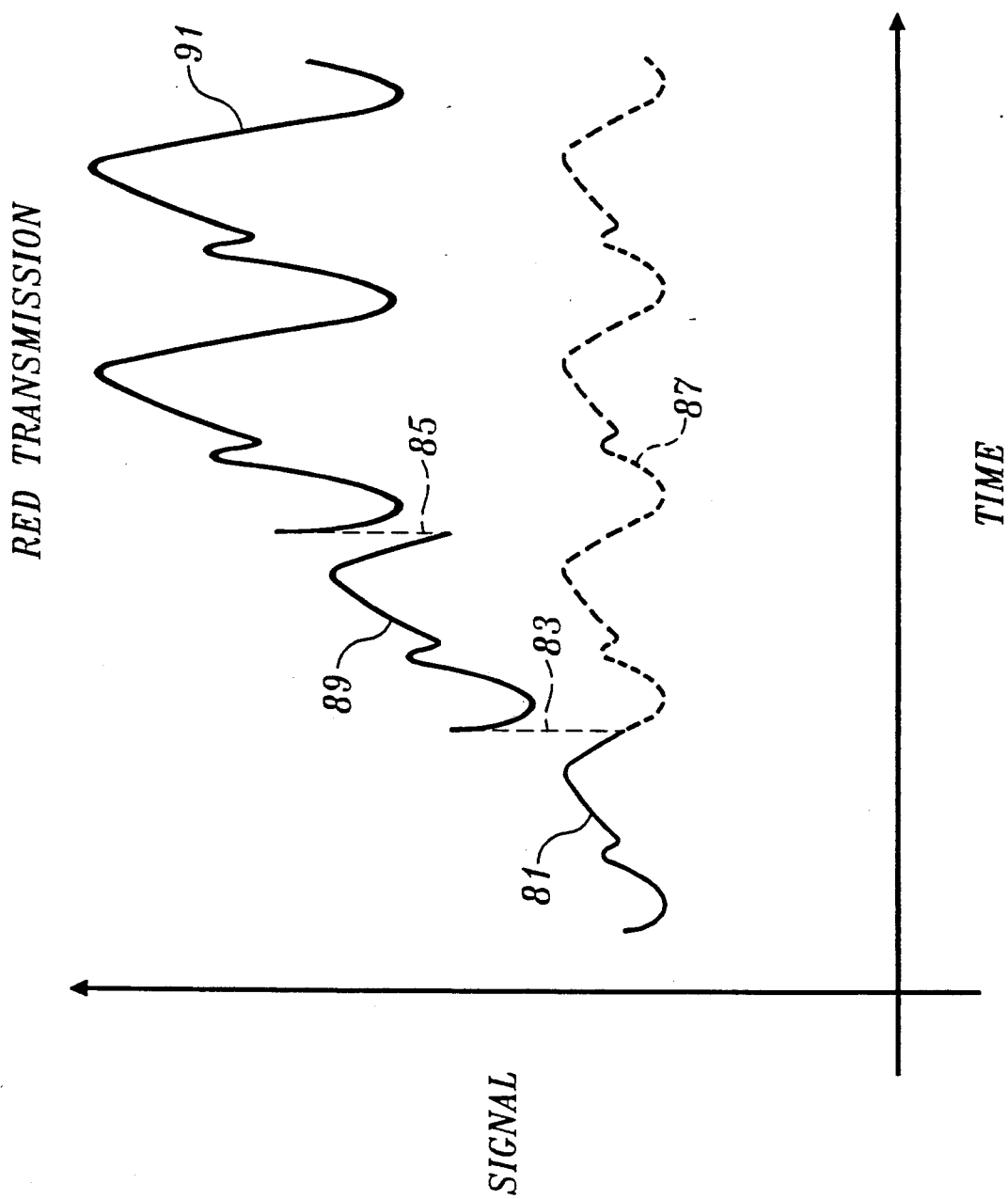
FIG. 4 is a graphical plot as a function of time of the transmittance of light at the red wavelength and having a discontinuities as a result of adjusting the intensity of the light output from the red LED.

For example, FIG. 4 illustrates a red transmission waveform that has two discontinuities. As seen, an initial waveform 81 charts the red transmittance pulses until a first discontinuity 83. The first discontinuity 83 is caused by a change in the intensity of the pulses of light output by red LED 21. In the particular case shown in FIG. 4, the intensity of the pulses of light output by red LED 21 is increased. Thus, subsequent red transmittance pulses will have a corresponding increased intensity and result in a first increased waveform 89. It has been found that the intensity of the transmittance pulses varies proportionally with the intensity of the pulses of light. Thus, if the intensity of the pulses of light output by the LEDs is increased by seventy-five percent, the intensity of the transmittance pulses is increased by seventy-five percent. Similarly, a second discontinuity 85 is caused by another change in the intensity of the pulses of light output by red LED 21. In the particular case shown in FIG. 4, the intensity of the pulses of light output by red LED 21 is increased once again. Red transmittance pulses that are subsequent in time to second discontinuity 85 will have an increased intensity and result in a second increased waveform 91.

The step of normalization of box 41 scales the first increased waveform 89 and second increased waveform 91 into a normalized waveform 87. Because normalized waveform 87 is substantially continuous with initial waveform 81, the software that implements the low-pass filtering of box 45 will operate correctly. In particular, normalization involves multiplying all of the subsequent discrete values of the red transmittance pulses comprising the first increased waveform 89 that follow the first discontinuity 83 by a red normalization coefficient.

The red normalization coefficient is the ratio between: (1) the value of the magnitude signal contained in the control signal provided to red driver 33 during the time period of the initial waveform 81 and (2) the value of the magnitude signal contained in the control signal provided to red driver 33 during the time period of the first increased waveform 89. As noted earlier, the intensity of the pulses of light output by red LED 21 is directly controlled by the value of the magnitude signal. Moreover, the intensity of the red transmittance pulses is proportional to the intensity of the pulses of light output by red LED 21. Therefore, the ratio of the value of the magnitude signals before and after the first discontinuity is representative of the ratio of the red transmittance pulses before and after the first discontinuity.

As a specific example, if the first discontinuity 83 is caused by a doubling of the value of the magnitude signal to red LED 21, the drive current $D_R$ output by red driver 33 will be doubled, and therefore the intensity of the pulses of red light output by red LED 21 is doubled. In turn, the intensity of the red transmittance pulses received by detector 13 is doubled. In order to remove the first discontinuity 83, the red transmittance pulses subsequent to the first discontinuity 83 that form the first increased waveform 89 must be multiplied by a red normalizing coefficient of 0.50. This results in the normalized waveform 87 that is substantially continuous with initial waveform 81.

A similar normalizing procedure occurs during the second discontinuity 85. In particular, the second discontinuity 85 occurs as a result of an increase in intensity of the pulses of light output by red LED 21. Thus, a revised red normalization coefficient must be determined, once again, as the ratio between: (1) the value of the magnitude signal contained in the control signal provided to red driver 33 during the time period of the initial waveform 81 and (2) the value of the magnitude signal contained in the control signal provided to red driver 33 during the time period of the second increased waveform 91. Assuming that the value of the magnitude signal provided by microprocessor 29 during the second increased waveform 91 is three times the value of the magnitude signal during the initial waveform 81, then the red normalization coefficient is 0.33.

In summary, each time an adjustment is made to the intensity of the pulses of light output by the red LED, the red normalization coefficient must be changed. Moreover, although a detailed description of the normalization procedure has been given in the context of a changing intensity of light output from the red LED 21, it can be appreciated that an analogous procedure is done if the intensity of the pulses of light output by infrared LED 23 is varied. Further, if there are no changes to the intensities of the pulses of light output from the LEDs, the normalizing step of box 41 is skipped. However, during normal operation of a pulse transmittance oximeter of the present invention, changes in the intensity of the pulses of light output from the LEDs may occur in accordance with the method of the present invention. For example, movement of the patient's finger 15 is one common activity that triggers the method of the present invention to adjust the LED intensity levels. During movement of the finger 15, the blood volume and thickness of the finger varies and therefore, the values of $R_H$, $R_L$, $IR_H$, and $IR_L$ will vary. As will be seen in greater clarity below, the LED intensity levels will vary if the measured values of $R_H$, $R_L$, $IR_H$, and $IR_L$ vary.

At a box 45, after the red and/or infrared transmission waveforms have been normalized so as to be substantially continuous, the waveforms are processed by a digital low-pass filter implemented as software in the microprocessor. The low-pass filters remove high-frequency noise from the red and infrared transmission waveforms. Following filtering at box 45, at a box 51, peak detection software within the memory of microprocessor 29 operates to determine the values of $R_H$, $R_L$, $IR_H$, and $IR_L$ for the next full cycle of the transmission waveforms. Various peak detection techniques and the software for implementing the same are known in the art. One such peak detection method is disclosed in U.S. Pat. No. 4,800,495 to Smith entitled "Method and Apparatus for Processing Signals Used in Oximetry".

Once the values of $R_H$, $R_L$, $IR_H$, and $IR_L$ are ascertained, at a block 52, the values of $R_H$, $R_L$, $IR_H$, and $IR_L$ are denormalized to the pre-normalization values prior to the normalization of box 41. This involves multiplying the values of $R_H$, $R_L$, $IR_H$, and $IR_L$ by a red denormalization coefficient defined to be the reciprocal of the red and/or infrared normalizing coefficients used in box 41. In the example above, during the time period of the first increased waveform 89, the red normalization coefficient was 0.50. Thus, the red denormalization coefficient for the time period of the first increased waveform 89 would be 2.00. Similarly, during the time period of the second increased waveform 91, the red normalization coefficient was 0.33. Thus, the red denormalization coefficient for the time period of the second increased waveform 91 would be 3.00. The step of denormalization is necessary to reverse the normalization process of box 41, provide a true indication of the output of detector 13, and thus the true values of $R_H$, $R_L$, $IR_H$, and $IR_L$ so that further processing in accordance of the present invention may be accomplished. It can be seen that the process of normalization and denormalization is performed primarily to allow the low-pass filtering software to operate upon the red and infrared transmission waveforms.

Next, at a box 53, the difference between $R_H$ and $R_L$ and the difference between $IR_H$ and $IR_L$ is calculated. The difference between $R_H$ and $R_L$, denoted by $\Delta R$, is defined as $\Delta R = R_H - R_L$. The difference between $IR_H$ and $IR_L$, denoted by $\Delta IR$, is defined as $\Delta IR = IR_H - IR_L$. Moreover, an adjustment factor K, defined as $K = \Delta R / \Delta IR$, is calculated.

The following described the preferred embodiment for using the values of K, $\Delta R$, and $\Delta IR$ to adjust the intensity of the LEDs. However, some observations regarding the physical characteristics of the individual components comprising the pulse transmittance oximeter 11 shown in FIG. 1 may be helpful in order to fully understand the operation of the present invention. As noted earlier, the LEDs 21 and 23 can emit light at different intensities. However, the LEDs are limited in their operating range. Specifically, the LEDs 21 and 23 have a maximum light output. Thus, driving current $D_R$ and $D_{IR}$ to LEDs 21 and 23 must be limited to values that keep the LEDs within operating range.

Similarly, it can be appreciated that the other components of the pulse transmittance oximeter 11 may have analogous operating limitations. For example, the drivers 31 and 33 must produce driving currents only within a predetermined operating range. Thus, although the magnitude signal provided by microprocessor 29 could attempt to instruct the driver to produce a large driving current, the driving current dictated by the magnitude signal may be outside the drivers predetermined operating range. As another example, the detector 13 may have an operating range, above and below which, the detector 13 does not operate correctly. Thus, it can be appreciated that the operating ranges of the components of oximeter 11 limit the operation of the oximeter 11 itself. In particular, the microprocessor 29 must provide control signals that have magnitude signals that dictate a drive current $D_R$ and $D_{IR}$ from the drivers 31 and 33 that are within their operating range. Similarly, the drive current $D_R$ and $D_{IR}$ must be within the acceptable range for driving the LEDs 21 and 23. In turn, the light output by the LEDs must be of such intensity so as to be within the operating range of detector 13.

The operation of the oximeter 11 such that all components are within their respective operating ranges is determined by the magnitude signals contained in the control signals. Based upon the specific components used for the LEDs 21 and 23, drivers 31 and 33, detector 13, and preamplifier 25, the microprocessor must provide magnitude signals that are within a predetermined range in order for the oximeter 11 as a whole to operate correctly. The predetermined range will be referred to herein as the magnitude signal range. In the preferred embodiment, the magnitude signal range is the same for both the red and infrared control signals. Although the present invention described the adjustment of the intensity of the pulses of light output by the LEDs, in the preferred embodiment described here, the adjustments are made by having microprocessor 29 change the magnitude signals. Moreover, the changes in the magnitude signals must be made such that the magnitude signals remain within the magnitude signal range.

Continuing with the description of FIG. 3, at a box 55, $\Delta R$ and $\Delta IR$ are compared to determine if they are substantially equivalent to one another. In the preferred embodiment, $\Delta R$ and $\Delta IR$ are considered substantially equivalent if the values are within five percent of one another. If the values of $\Delta R$ and $\Delta IR$ are substantially equivalent, at a box 67, $R_{OS}$ in accordance with prior art Eq. (1) is calculated. The calculated value of $R_{OS}$ is then transmitted to a display for use by medical personnel.

If the values of $\Delta R$ and $\Delta IR$ are not substantially equivalent, the method of the present invention, at boxes 57–65, operates to adjust the magnitude signals contained in subsequent red and infrared control signals until the values of $\Delta R$ and $\Delta IR$ are substantially equivalent, while maintaining the oximeter 11 within its operating range. First, at a decision box 57, the value of adjustment factor K is analyzed. If the value of the adjustment factor K is greater than one, a decision box 59 is executed. At box 59, if the magnitude signal contained in the current infrared control signals can be multiplied by the adjustment factor K and still be within the magnitude signal range, then at a box 61, the magnitude signal contained in subsequent infrared control signals is multiplied by the adjustment factor K. This in turn will cause, via the infrared driver 31, the intensity of the pulses of light output by infrared LED 23 to be multiplied by K.

If the magnitude signal contained in the current infrared control signals cannot be multiplied by the adjustment factor K and still be within the magnitude signal range, then at a box 63, the magnitude signal contained in subsequent red control signals is divided by the adjustment factor K. Following completion of boxes 61 or 63, $R_{OS}$ in accordance with prior art Eq. (1) is calculated and transmitted for display at box 67.

If, however at box 57, the adjustment factor K is not greater than one, a decision box 65 is executed. At box 65, if the magnitude signal contained in the current red control signals can be divided by the adjustment factor K and still be within the magnitude signal range, then at box 63, the magnitude signal contained in subsequent red control signals is divided by the adjustment factor K. Note that because the adjustment factor K is less than one, the intensity of the pulses of light output by red LED 21 will actually be increased. If the magnitude signal contained in the current red control signals cannot be divided by the adjustment factor K and still be within the magnitude signal range, then at box 61, the magnitude signal contained in subsequent infrared control signals is multiplied by the adjustment factor K. As noted above, following completion of boxes 61 or 63, $R_{OS}$ in accordance with prior art Eq. (1) is calculated and transmitted for display at box 67.

After completion of box 67, the operation of microprocessor 29 returns to box 41 to repeat the process of boxes 41-67 for the next cycle of the red and infrared transmission waveforms. By the iterative routine of boxes 41-67, the intensity of the light output from red LED 21 and infrared LED 23 is adjusted such that $\Delta R$ is substantially equal to $\Delta IR$. Moreover, because of the adjustment factor K, only one adjustment is needed. Further, the adjustment of the LEDs is done in a manner that is non-disruptive to the low-pass filtering.

Adjusting the output of LEDs 21 and 23 such that $\Delta R = \Delta IR$ results in a noise insensitive pulse transmittance oximeter. To appreciate this result, we must return to the equation for oxygen saturation ratio, given above as Eq. (1):

$$R_{OS} = \frac{\ln\left(\frac{R_H}{R_L}\right)}{\ln\left(\frac{IR_H}{IR_L}\right)}$$

Eq. (1) may be rewritten as:

$$R_{OS} = \frac{\ln\left(\frac{R_L + \Delta R}{R_L}\right)}{\ln\left(\frac{IR_L + \Delta IR}{IR_L}\right)} \tag{2}$$

where $R_H = R_L + \Delta R$ and $IR_H = IR_L + \Delta IR$.

Typically, $\Delta R << R_L$ and $\Delta IR << IR_L$. Therefore, the approximations $$\ln\left(\frac{R_L + \Delta R}{R_L}\right) \approx \frac{\Delta R}{R_L} \tag{3}$$

and $$\ln\left(\frac{IR_L + \Delta IR}{IR_L}\right) \approx \frac{\Delta IR}{IR_L}$$

may be made. Substituting Eq. (3) into Eq. (2) results in:

$$R_{OS} \approx \frac{\frac{\Delta R}{R_L}}{\frac{\Delta IR}{IR_L}} \tag{4}$$

Eq. (4) may be rewritten as:

$$R_{OS} \approx \left(\frac{IR_L}{R_L}\right)\left(\frac{\Delta R}{\Delta IR}\right) \tag{5}$$

In the foregoing analysis, we have not accounted for noise in the measurements of $R_H$, $R_L$, $IR_H$, and $IR_L$. To account for noise, we assume that an arbitrary amount of noise is added to $R_H$, $R_L$, $IR_H$, and $IR_L$, denoted as $\epsilon_{RH}$, $\epsilon_{RL}$, $\epsilon_{IRH}$, and $\epsilon_{IRL}$, respectively. Eq. (5) then becomes:

$$R_{OS,NOISE} = \left(\frac{IR_L + \epsilon_{IRL}}{R_L + \epsilon_{RL}}\right)\left(\frac{(R_H + \epsilon_{RH}) - (R_L + \epsilon_{RL})}{(IR_H + \epsilon_{IRH}) - (IR_L + \epsilon_{IRL})}\right) \tag{6}$$

Eq. (6) may be rewritten as:

$$R_{OS,NOISE} = \left(\frac{IR_L + \epsilon_{IRL}}{R_L + \epsilon_{RL}}\right)\left(\frac{\Delta R + \epsilon_{RH} - \epsilon_{RL}}{\Delta IR + \epsilon_{IRH} - \epsilon_{IRL}}\right) \tag{7}$$

If $$\Delta R = \Delta IR \tag{8}$$

and $$\epsilon_{RH} - \epsilon_{RL} = \epsilon_{IRH} - \epsilon_{IRL} \tag{9}$$

then Eq. (7) may be rewritten as:

$$R_{OS,NOISE} = \left(\frac{IR_L + \epsilon_{IRL}}{R_L + \epsilon_{RL}}\right) \tag{10}$$

In the method of the present invention, the condition of Eq. (8) is carried out by microprocessor 29 in performing the iterative routine illustrated in FIG. 3. In particular, microprocessor 29 controls the intensity of red LED 21 and infrared LED 23 such that $\Delta R = \Delta IR$. The condition of Eq. (9) is satisfied when:

$$\epsilon_{RH} = \epsilon_{IRH}$$

and $$\epsilon_{RL} = \epsilon_{IRL} \tag{11}$$

Referring back to FIG. 2, it can be seen that the measurements of $R_H$ and $IR_H$ are taken at substantially the same time. It has been found that with pulse transmittance oximeters that share common processing circuitry, as exemplified by the oximeter of FIG. 1, the noise is typically the same for both $R_H$ and $IR_H$. Similarly, the measurements of $R_L$ and $IR_L$ are taken at substantially the same time. Thus, the noise is typically the same for both $IR_L$ and $IR_L$. Moreover, for the condition of $R_L >> \epsilon_{RL}$ and $IR_L >> \epsilon_{IRL}$, Eq. (10) can be approximated as:

$$R_{OS,NOISE} = \left(\frac{IR_L}{R_L}\right) \quad (12)$$

Eq. (12) reveals that the calculation of the oxygen saturation ratio is independent of noise. Thus, by controlling red LED 21 and infrared LED 23 such that $\Delta R = \Delta IR$, the oxygen saturation ratio calculation is insensitive to noise.

An analysis of Eq. (7) indicates that an alternative embodiment of the present invention exists. For the preferred embodiment, the result of Eq. (10) is reached when the conditions of Eqs. (8-9) are satisfied. However, it can be seen from Eq. (7) that the result of Eq. (10) can also be reached when the following condition is met:

$$\Delta R/\Delta IR = (\epsilon_{RH} - \epsilon_{RL})/(\epsilon_{IRH} - \epsilon_{IRL}) \quad (13)$$

Stated in words, when the ratio of the difference in errors between the diastolic and systolic measurements for the red light:

$$(\epsilon_{RH} - \epsilon_{RL})$$

and the difference in errors between the diastolic and systolic measurements for the infrared light:

$$(\epsilon_{IRH} - \epsilon_{IRL})$$

is equivalent to the ratio of $\Delta R$ to $\Delta IR$, Eq. (10) holds and the pulse transmittance oximeter will be insensitive to noise. The right side of Eq. (13) is called a noise ratio and denoted, $R_n$. Thus, in an alternative embodiment of the present invention, when the ratio of $\Delta R$ and $\Delta IR$ is equal to the noise ratio $R_n$, the pulse transmittance oximeter is also noise insensitive. Normally, in a pulse transmittance oximeter where the red and infrared transmittance pulses are processed by common circuitry, the noise ratio $R_n$ is equivalent to one. This is the case in the preferred embodiment. However, in certain pulse transmittance oximeters where the processing circuitry is different for the red and infrared transmittance pulses, the noise ratio $R_n$ is typically not equal to one.

Figure 5:
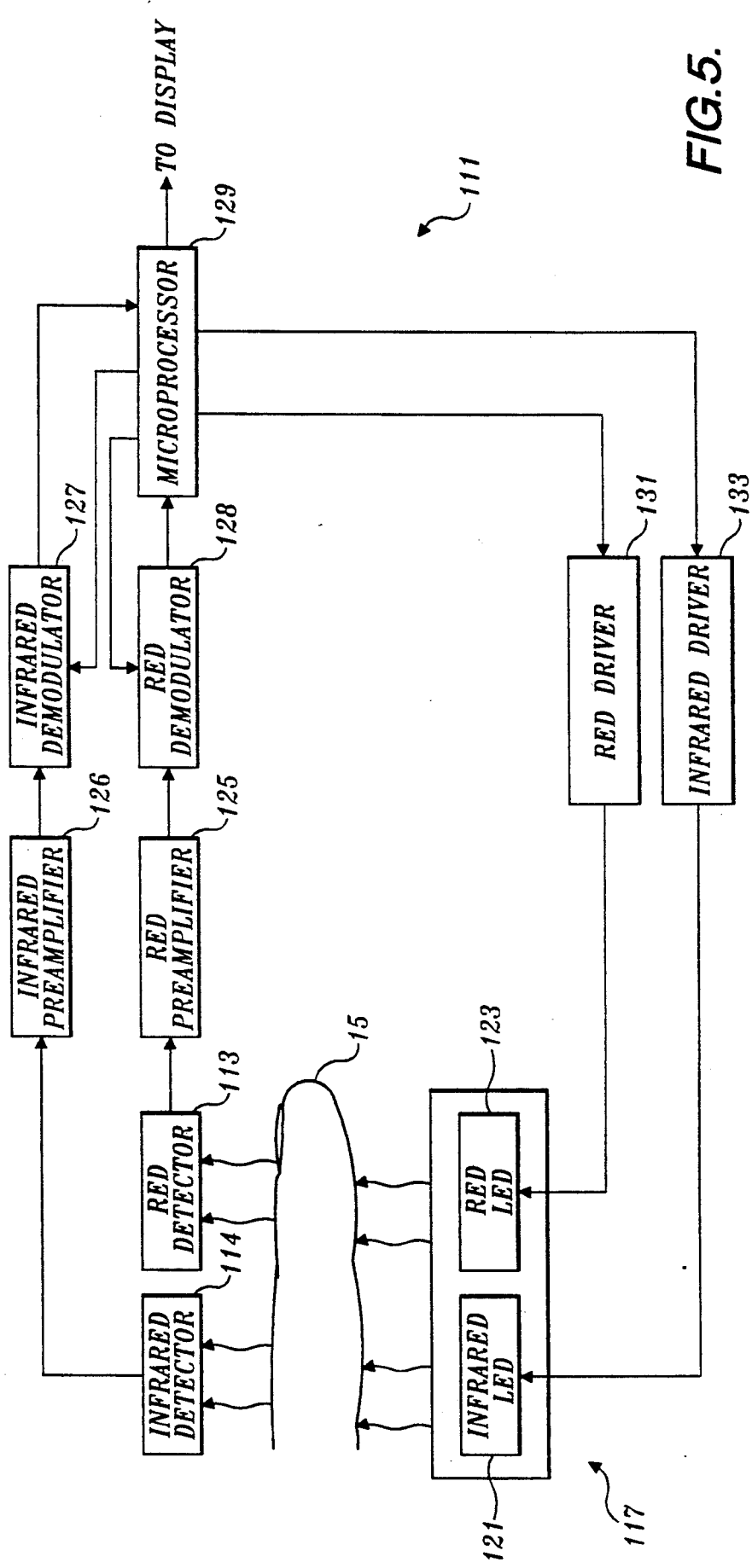
FIG. 5 is a block diagram of an alternative embodiment of a pulse transmittance oximeter.

For example, as seen in FIG. 5, an alternative embodiment of a pulse transmittance oximeter 111 is seen. The composition and operation of the oximeter 111 is similar to that of oximeter 11 shown in FIG. 1. Pulse transmittance oximeter 111 comprises a light source 117, a red detector 113, an infrared detector 114, a red preamplifier 125, an infrared preamplifier 126, a red demodulator 128, an infrared demodulator 127, a microprocessor 129, a red driver 133, and an infrared driver 131. The light source 117 includes a red LED 123 and an infrared LED 121. Red LED 123 produces red light in the red region of the electromagnetic spectrum. Infrared LED 121 produces infrared light in the infrared region of the electromagnetic spectrum.

In operation, microprocessor 129 supplies red control signals to red driver 133 and infrared control signals to infrared driver 131. The red control signals and the infrared control signals are transmitted in alternating sequence. Each time a red control signal is received by red driver 133, red driver 133 produces a red driving current $D_R$ that causes red LED 123 to emit a pulse of red light. Similarly, each time an infrared control signal is received by infrared driver 131, infrared driver 131 produces an infrared driving current $D_{IR}$ that causes infrared LED 121 to emit a pulse of infrared light. Thus, the control signals cause the drivers 131 and 133 to produce a driving current that causes the LEDs to emit a pulse of light.

Moreover, both the red and infrared control signals has integrated therein a magnitude signal that determines the magnitude of the driving currents $D_R$ and $D_{IR}$ produced by the drivers 131 and 133. The magnitude signal is integrated into the control signals by microprocessor 129. The magnitude of the driving currents $D_R$ and $D_{IR}$ supplied by drivers 131 and 133 to the LEDs determines the intensity of the pulses of light that are output. The larger the driving current supplied to the LEDs, the greater the intensity of the pulses of light produced. The LEDs utilized respond linearly to the driving current. For example, if the driving current is doubled, the intensity of the light produced by the LED is doubled. Thus, the microprocessor 129 can directly and accurately control the intensity of the pulses of light output by the LEDs by controlling the formulation of the magnitude signal. Conversely, the intensity of the pulses of light output by the LEDs can be determined by examining the magnitude signal provided by microprocessor 129.

The pulses of red light and the pulses of infrared light are directed towards and transmitted through tissue having blood flowing therein, such as a finger 15. The pulses of red light that are transmitted through finger 15 are received by red detector 113 as red transmittance pulses. The pulses of infrared light that are transmitted through finger 15 are received by infrared detector 114 as infrared transmittance pulses. In turn, red detector 113 provides an output signal that is indicative of the intensity of the red transmittance pulses incident thereon and infrared detector 114 provides an output signal that is indicative of the intensity of the infrared transmittance pulses incident thereon.

The output signal produced by red detector 113 is provided to red preamplifier 125 which serves to amplify the red detector output signal. The output signal produced by infrared detector 114 is provided to infrared preamplifier 126 which serves to amplify the infrared detector output signal. The output of red preamplifier 125 is supplied to red demodulator 128 as a red demodulator input signal. The output of infrared preamplifier 126 is supplied to infrared demodulator 127 as an infrared demodulator input signal. Red demodulator 128 operates to produce red transmission waveforms. Infrared demodulator 127 operates to produce infrared transmission waveforms. Exemplary of the waveforms that may be produced are those shown in FIG. 2. Although the red and infrared waveforms of FIG. 2 are shown as continuous, the waveforms are comprised of a series of discrete values. Each discrete value corresponds to a single red or infrared transmittance pulse. For clarity however, the discrete values have been connected so as to form the continuous red and infrared waveforms of FIG. 2.

The effect of having different processing circuitry for the red and infrared transmittance pulses is that the noise components in the transmittance pulses are different. In particular, in the preferred embodiment described above, $$\epsilon_{RH} = \epsilon_{IRH}$$

and $$\epsilon_{RL} = \epsilon_{IRL}$$

However, where the red transmittance pulses and the infrared transmittance pulses are processed in different circuitry, it has been found that the above conditions are not readily satisfied. In such a case, in the alternative embodiment, the ratio of $\Delta R$ over $\Delta IR$ is made equal to the noise ratio $R_n$.

Figure 6:
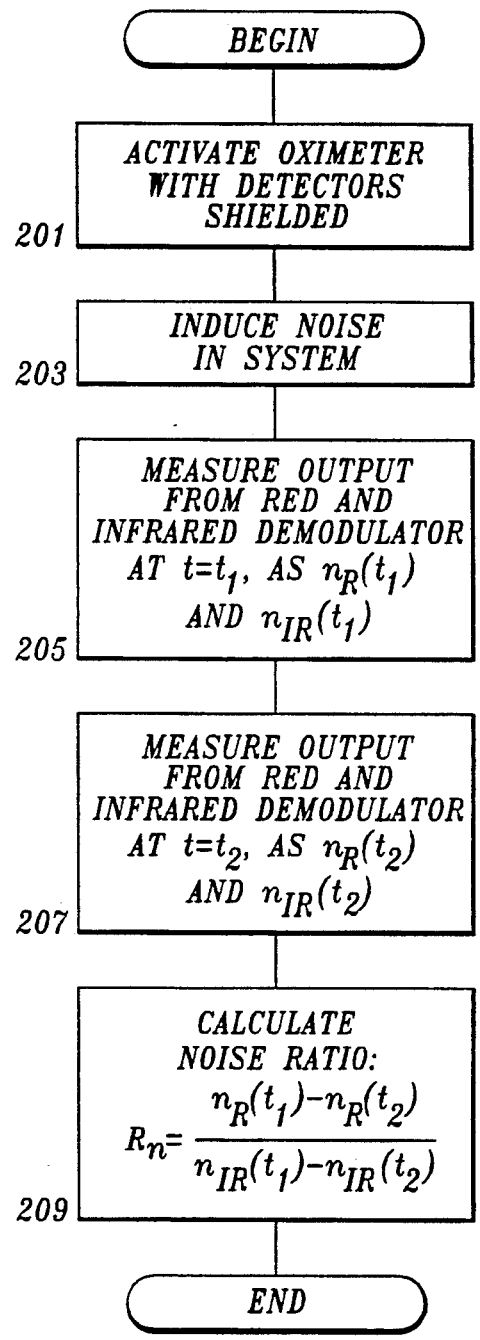
FIG. 6 is a flow chart illustrating the preferred method of empirically determining the noise ratio of an oximeter.

Determination of the noise ratio for oximeter 111 is accomplished by empirical means. Specifically, FIG. 6 illustrates one preferred method of determining the noise ratio for oximeter 111. At a box 201, oximeter 111 is activated as in normal operation described above. However, the red detector 113 and the infrared detector 114 are completely shielded from light. Next, at a box 203, noise is induced into the oximeter 111. One method to induce noise is to lay alongside the oximeter 111 an electrical cable carrying a square wave repeating at one Hertz. The square wave signal tends to induce a wide frequency spectrum of noise into the processing circuitry of the oximeter 111. It has been found that the noise induced in this manner is effective in determining the noise ratio.

Next, at a box 205, the output of the red demodulator 128 is measured at an time $t_1$ and denoted $n_r(t_1)$. Similarly, the output of the infrared demodulator 127 is measured at the same time $t_1$ and denoted $n_{ir}(t_1)$. The time $t_1$ is arbitrary, as long as it is after the oximeter 111 has been activated and is in normal operation. Next, at a box 207, the output of the red demodulator 128 is measured at an time $t_2$ and denoted $n_r(t_2)$. Similarly, the output of the infrared demodulator 127 is measured at the same time $t_2$ and denoted $n_{ir}(t_2)$. The time $t_2$ is also arbitrary, as long as it is after time $t_1$. Finally, at a box 209, the noise ratio $R_n$ is equal to $[n_r(t_1) - n_{ir}(t_1)]/[n_r(t_2) - n_{ir}(t_2)]$. It has been found that empirical determination of the noise ratio $R_n$ in accordance with the above method is a good estimation of the actual noise ratio. After the noise ratio $R_n$ has been determined in accordance with FIG. 6, in operation, oximeter 111 continually adjusts the intensity of the pulses of light output by red LED 121 and infrared LED 123 until the ratio of $\Delta R$ over $\Delta IR$ is substantially equal to the noise ratio $R_n$.

While the preferred embodiment of the invention has been illustrated and described, it will be appreciated that various changes can be made therein without departing from the spirit and scope of the invention. Thus, the present invention may be practiced other than as specifically disclosed herein.

The embodiments of the invention in which an exclusive property or privilege is claimed are defined as follows:

1. A method for desensitizing a pulse transmittance oximeter to noise, said pulse transmittance oximeter including a first light source emitting light of a first wavelength and a second light source emitting light of a second wavelength, said method comprising the steps of:

(a) measuring the transmittance of said light of a first wavelength and the transmittance of said light of a second wavelength through tissue having arterial blood flowing therein at substantially a first time instant, said first time instant corresponding to systolic pressure in said tissue;

(b) measuring the transmittance of said light of a first wavelength and the transmittance of said light of a second wavelength through said tissue at substantially a second time instant, said second time instant corresponding to diastolic pressure in said tissue;

(c) calculating a first differential as the difference between the transmittance of said light of a first wavelength through said tissue at said first time instant and at said second time instant and calculating a second differential as the difference between the transmittance of said light of a second wavelength through said tissue at said first time instant and at said second time instant; and (d) adjusting the intensity of said first light source and said second light source until said first differential is substantially equivalent to said second differential.

2. The method of claim 1 wherein the step of adjusting comprises:

increasing the intensity of said first light source if said first differential is less than said second differential and the increased intensity of said first light source remains within a first predetermined intensity range; and increasing the intensity of said second light source if said second differential is less than said first differential and the increased intensity of said second light source remains within a second predetermined intensity range.

3. The method of claim 2 wherein after the step of adjusting the intensity of said light sources, the method further including the step of normalizing the transmittance of said light of a first wavelength, if the intensity of said first light source is increased.

4. The method of claim 2 wherein after the step of adjusting the intensity of said light sources, the method further including the step of normalizing the transmittance of said light of a second wavelength, if the intensity of said second light source is increased.

5. The method of claim 1 further including the step of calculating an adjustment factor as the ratio of said first differential and said second differential and wherein said step of adjusting comprises:

increasing in proportion to the reciprocal of said adjustment factor the intensity of said first light source if said increased intensity of said first light source remains within a first predetermined range and said adjustment factor is less than one;

decreasing in proportion to said adjustment factor the intensity of said second light source if said increased intensity of said first light source is without said first predetermined range and said adjustment factor is less than one;

increasing in proportion to said adjustment factor the intensity of said second light source if said increased intensity of said second light source remains within a second predetermined range and said adjustment factor is greater than one; and decreasing in proportion to the reciprocal of said adjustment factor the intensity of said first light source if said increased intensity of said second light source is without said second predetermined range and said adjustment factor is greater than one.

6. The method of claim 5 wherein after the step of adjusting the intensity of said light sources, the method further including the step of normalizing the transmittance of said light of a first wavelength, if the intensity of said first light source is increased or decreased.

7. The method of claim 5 wherein after the step of adjusting the intensity of said light sources, the method further including the step of normalizing the transmittance of said light of a second wavelength, if the intensity of said second light source is increased or decreased.

8. The method of claim 1 wherein said light of a first wavelength is in the red region of the electromagnetic spectrum and said light of a second wavelength is in the infrared region of the electromagnetic spectrum.

9. An apparatus for desensitizing a pulse transmittance oximeter to noise, said pulse transmittance oximeter including a first light source means for emitting light of a first wavelength and a second light source means for emitting light of a second wavelength, said apparatus comprising:
(a) means for measuring the transmittance of said light of a first wavelength and said light of a second wavelength through tissue having arterial blood flowing therein at substantially a first time instant, said first time instant corresponding to systolic pressure in said tissue, and at substantially a second time instant, said second time instant corresponding to diastolic pressure in said tissue;
(b) means for calculating a first differential as the difference between the transmittance of said light of a first wavelength through said tissue at said first time instant and at said second time instant and calculating a second differential as the difference between the transmittance of said light of a second wavelength through said tissue at said first time instant and at said second time instant; and
(c) control means for adjusting the intensity of said first light source and said second light source until said first differential is substantially equivalent to said second differential.

10. The apparatus of claim 9 wherein said control means includes:
means for increasing the intensity of said first light source if said first differential is less than said second differential and the increased intensity of said first light source remains within a first predetermined intensity range; and
means for increasing the intensity of said second light source if said second differential is less than said first differential and the increased intensity of said second light source remains within a second predetermined intensity range.

11. The apparatus of claim 9 further including means for determining an adjustment factor as the ratio of said first differential and said second differential, and wherein said control means includes:
means for increasing in proportion to the reciprocal of said adjustment factor the intensity of said first light source if said increased intensity of said first light source remains within a first predetermined range and said adjustment factor is less than one;
means for decreasing in proportion to said adjustment factor the intensity of said second light source if said increased intensity of said first light source is without said first predetermined range and said adjustment factor is less than one;
means for increasing in proportion to said adjustment factor the intensity of said second light source if said increased intensity of said second light source remains within a second predetermined range and said adjustment factor is greater than one; and
means for decreasing in proportion to the reciprocal of said adjustment factor the intensity of said first light source if said increased intensity of said second light source is without said second predetermined range and said adjustment factor is greater than one.

12. The apparatus of claim 11 further including normalizing means for normalizing the transmittance of said light of a first wavelength, if the intensity of said first light source is increased or decreased, and normalizing the transmittance of said light of a second wavelength, if the intensity of said second light source is increased or decreased.

13. A method for desensitizing a pulse transmittance oximeter to noise, said pulse transmittance oximeter including a first light source emitting light of a first wavelength and a second light source emitting light of a second wavelength, said method comprising the steps of:
(a) measuring the transmittance of said light of a first wavelength and the transmittance of said light of a second wavelength through tissue having arterial blood flowing therein at substantially a first time instant, said first time instant corresponding to systolic pressure in said tissue;
(b) measuring the transmittance of said light of a first wavelength and the transmittance of said light of a second wavelength through said tissue at substantially a second time instant, said second time instant corresponding to diastolic pressure in said tissue;
(c) calculating a first differential as the difference between the transmittance of said light of a first wavelength through said tissue at said first time instant and at said second time instant and calculating a second differential as the difference between the transmittance of said light of a second wavelength through said tissue at said first time instant and at said second time instant; and
(d) adjusting the intensity of said first light source and said second light source until the ratio of said first differential to said second differential is substantially equivalent to a noise ratio.

14. The method of claim 13 wherein said noise ratio is defined to be the ratio of a first error differential to a second error differential,
said first error differential defined as the difference between the error in said transmittance of said light of a first wavelength through said tissue at said first time instant and said transmittance of said light of a first wavelength at said second time instant, and
said second error differential defined as the difference between the error in said transmittance of said light of a second wavelength through said tissue at said first time instant and said transmittance of said light of a second wavelength at said second time instant.

15. An apparatus for desensitizing a pulse transmittance oximeter to noise, said pulse transmittance oximeter including a first light source means for emitting light of a first wavelength and a second light source means for emitting light of a second wavelength, said apparatus comprising:
(a) means for measuring the transmittance of said light of a first wavelength and said light of a second wavelength through tissue having arterial blood flowing therein at substantially a first time instant, said first time instant corresponding to systolic pressure in said tissue, and at substantially a second time instant, said second time instant corresponding to diastolic pressure in said tissue;
(b) means for calculating a first differential as the difference between the transmittance of said light of a first wavelength through said tissue at said first time instant and at said second time instant and calculating a second differential as the difference between the transmittance of said light of a second wavelength through said tissue at said first time instant and at said second time instant; and
(c) control means for adjusting the intensity of said first light source and said second light source until the ratio of said first differential to said second differential is substantially equivalent to a noise ratio.

16. The apparatus of claim 15 further including noise ratio means for determining said noise ratio, said noise ratio defined to be the ratio of a first error differential to a second error differential,
said first error differential defined as the difference between the error in said transmittance of said light of a first wavelength through said tissue at said first time instant and said transmittance of said light of a first wavelength at said second time instant, and
said second error differential defined as the difference between the error in said transmittance of said light of a second wavelength through said tissue at said first time instant and said transmittance of said light of a second wavelength at said second time instant.

17. A method for measuring an oxygen saturation ratio comprising the steps of:
(a) transmitting through tissue having arterial blood flowing therein light of a first wavelength and light of a second wavelength;
(b) measuring the transmittance of light at said first wavelength and the transmittance of light at said second wavelength at both systolic pressure and diastolic pressure, wherein the transmittance of light at said first wavelength at systolic pressure is denoted by $R_L$, the transmittance of light at said first wavelength at diastolic pressure is denoted by $R_H$, the transmittance of light at said second wavelength at systolic pressure is denoted by $IR_L$, and the transmittance of light at said second wavelength at diastolic pressure is denoted by $IR_H$;
(c) determining a $\Delta R$ parameter and a $\Delta IR$ parameter, said $\Delta R$ and said $\Delta IR$ parameters defined as $\Delta R = R_H - R_L$ and $\Delta IR = IR_H - IR_L$;
(d) adjusting the intensity of said light of a first wavelength until $\Delta R$ is substantially equivalent to $\Delta IR$; and
(e) calculating the oxygen saturation ratio from $R_H$, $R_L$, $IR_H$, and $IR_L$.

18. An apparatus for measuring an oxygen saturation ratio comprising:
(a) a first light source means for transmitting through tissue having arterial blood flowing therein light of a first wavelength;
(b) a second light source means for transmitting through tissue having arterial blood flowing therein light of a second wavelength;
(c) means for measuring the transmittance of light at said first wavelength and the transmittance of light at said second wavelength at both systolic pressure and diastolic pressure, wherein the transmittance of light at said first wavelength at systolic pressure is denoted by $R_L$, the transmittance of light at said first wavelength at diastolic pressure is denoted by $R_H$, the transmittance of light at said second wavelength at systolic pressure is denoted by $IR_L$, and the transmittance of light at said second wavelength at diastolic pressure is denoted by $IR_H$;
(d) microprocessor means for determining a $\Delta R$ parameter and a $\Delta IR$ parameter, said $\Delta R$ and said $\Delta IR$ parameters defined as $\Delta R = R_H - R_L$ and $\Delta IR = IR_H - IR_L$;
(d) control means for adjusting said first and second light sources such that $\Delta R$ is substantially equivalent to $\Delta IR$; and
(e) calculator means for determining said oxygen saturation ratio from $R_L$, $R_H$, $IR_L$, and $IR_H$.

* * * * *